United States Patent [19]

Kapp et al.

[11] Patent Number: 5,054,497
[45] Date of Patent: Oct. 8, 1991

[54] CRANIAL SENSOR ATTACHING DEVICE AND METHOD FOR ITS USE

[75] Inventors: John P. Kapp, Galax, Va.; Albert B. Cecchini, Jamestown, N.Y.

[73] Assignee: Biomedical Monitors and Implants, Inc., Galax, Va.

[21] Appl. No.: 483,555

[22] Filed: Feb. 21, 1990

[51] Int. Cl.[5] .............................................. A61B 5/03
[52] U.S. Cl. .................................... 128/748; 128/889
[58] Field of Search ....................... 128/748, 887, 774; 606/108

[56] References Cited

U.S. PATENT DOCUMENTS

| | | |
|---|---|---|
| 4,062,354 | 12/1977 | Taylor et al. |
| 4,233,979 | 11/1980 | Nasar |
| 4,265,252 | 5/1981 | Chubbuck et al. ................. 128/748 |
| 4,438,773 | 3/1984 | Letterio |
| 4,494,411 | 1/1985 | Koschke et al. |
| 4,572,212 | 2/1986 | Letterio |
| 4,646,752 | 3/1987 | Swann |
| 4,705,499 | 11/1987 | Hooven ................................... 604/9 |
| 4,805,643 | 2/1989 | Ullrich et al. |

OTHER PUBLICATIONS

Schettini et al., "Experimental Approach for Monitoring Brain Surface pressure," *Journal of Neurosurgery*, vol. 34, 1971, pp. 38–47.

Tindall et al., "Evaluation of a Subdural Pressure Transducer. Technical Note," *Journal of Neurosurgery*, vol. 37, 1972, pp. 117–121.

Vries et al., "A Subarachnoid Screw for Monitoring Intracranial Pressure," *Journal of Neurosurgery*, vol. 39, 1973, pp. 416–419.

Ivan, et al., "Intracranial Pressure Monitoring with the Fiberoptic Transducer in Children," *Child's Brain*, vol. 7, 1980, pp. 303–313.

*Primary Examiner*—Kyle L. Howell
*Assistant Examiner*—Kevin Pontius

[57] ABSTRACT

A sensor attaching device and a method for monitoring physiological pressure and other physiological parameters by application of an external pressure sensor to the surface of the brain is disclosed. The cranial sensor attaching device consists of a series of concentric cylinders, two of which have flanged ends configured in such manner that the flanged end of the outer cylinder expands radially when the flanged end of the inner cylinder is withdrawn through it. This feature prevents the device, once inserted through a hole in the skull, from being withdrawn. The flange on the outer cylinder is configured so that when inserted and expanded it contacts the inner lip (table) of the skull at three equidistant points around the circumference of the hole, thus assuring that the tip of the sensor is positioned tangential to the surface of the brain. A finger nut over the outer cylinder is tightened against the outer table of the skull, securing the device in place so that it cannot be pushed into the brain or rotated within the hole. The end-sensitive sensor is inserted into the inner cylinder and held in position by a screw cap, which protrudes through an incision in the skin. This allows the sensor to be removed for inspection, calibration, or replacement without removing the attaching device from the skull.

6 Claims, 2 Drawing Sheets

CRANIAL SENSOR ATTACHING DEVICE AND METHOD FOR ITS USE

BACKGROUND OF THE INVENTION

This invention relates to a device which holds a cylindrical end-sensitive sensor of the variety in commerial use for measuring pressure or other physiological functions. The device securely connects the sensor to the skull in such relationship to the brain as to provide for optimal electronic moitioring of brain surface pressure.

Intracranial pressure has been measured by catheters connecting the fluid within the cerebral ventricles to a variety of electronic and non-electronic pressure monitors, and brain tissue pressure has been measured by placing small transducers within the tissues of the brain. In order to avoid penetration of the brain by the monitoring device, brain surface pressure has been measured by hydraulically linking a fluid pool trapped beneath the skull with a pressure transducer located outside the skull. With this method leakage of coupling fluid or obstruction of the coupling channel by tissue often results in inaccurate measurements. To avoid the problems with fluid coupling, a variety of intracranial pressure measuring devices have been designed which allow the pressure sensor to be positioned in the space between the brain and the skull, with the wire leading from the sensor to the electronic reading device exiting the skull through a drilled insertion hole beside the sensor. Orientation of the pressure sensitive surface of such devices is uncertain. After these devices have been implanted, a second surgical operation is required to inspect, calibrate, or replace the sensor.

The use of end-sensitive pressure sensors applied to the membrane which covers the surface of the brain, the dura mater, and positioned tangential to the surface of the brain has been described. Certain devices used for such measurement have secured the pressure sensitive surface of the transducer the the skull by screw threads in the bone, by expansion of a pressfit ring surrounding the transducer to snugly fit the hole in the skull. Neither arrangement provides for non-surgical removal of the transducer. Additionally, none assures correct placement of the pressure sensitive surface at the critical depth beneath the skull, nor assures that, in the event of a tilted hole the pressure sensitive surface will be applied in a tangential manner to the surface of the brain. Furthermore, the screw-thread device is associated with the risk of bone chips being driven ahead of the male screw. In addition to the potential of chip penetration, displacement of the surface of the brain away from the pressure sensitive surface of the transducer by the chips results in an inaccurate pressure reading.

Certain sensor holders or anchoring devices are supplied in the form of cylinders which fit into a hole in the skull. An outer flange on the cylinder larger than the hole in the skull limits the depth of penetration of the cylinder into the hole in th skull. Such devices have been described in U.S. Pat. Nos. 4,265,252 and 4,705,499. These devices do not allow for the irregularity in the contour of the inner or outer tables of the skull, or for the normal variation in thickness of the skull in different individuals, and therefore do not assure that contact between the sensitive surface of the sensor and the dura mater is proper for accurate pressure measurement.

Other sensor anchoring devices incorporating lugs or cams on the tip of the anchoring device which engage the inner table of the skull and prevent withdrawal of the sensor tip through the hole have been described in U.S Pat. Nos. 4,062,354; 4,494,411; and 4,805,634. All of these devices require that the hole in the skull by precisely and uniquely tailored to accommodate the sensor anchoring device. This is a direct result of their inability to self-adjust to the varying conditions of skull thickness, hole configuration and simple surgical technique.

In the anchoring device of U.S. Pat. No. 4,062,354 side enlargements to the hole are required to permit passage of the lugs through the hole. The holding bracket is rotated after insertion to bring the lugs against the inner table of the skull. An internally threaded ring is then screwed onto outer threads on the anchoring device and tightened against the outer table of the skull, the skull thereby being clamped between the lugs and the ring.

In the anchoring devices of U.S. Pat. Nos. 4,494,411 and 4,805,634 a cylinder having spring ribs with beads on their ends is inserted through the hole. The ribs are forced outward by inserting a second cylinder or a cylindrical sensor into the anchoring device. Both of these anchoring devices require that a hole with two different diameters, a larger outer hole abruptly reduced to a smaller diameter inner hole be drilled through the skull. The precise depth of the sensor tip is determined by the distance between the inner table of the skull and the bottom of the outermost hole.

In summary, prior art for measurement of intracranial pressure requires penetration of the sensor into the brain; or measurement of pressure in a pocket of trapped fluid which may dissipate; or placement of a sensor between the skull and the brain, with the risk of improper orientation of the sensor, or use of a sensor anchored to the skull with a device which may drive bone chips ahead of it toward the brain when it is applied, which may not correctly orient the sensor, or which requires absolute technical precision and custom instruments for surgical placement. Furthermore, the anchoring devices of proir art require a second surgical procedure to remove the sensor for calibration or replacement. The method for measurement of intracranial pressure described herein and the sensor anchoring device of this application are designed to avoid the problems enumerated with the aforementioned methods of intracranial pressure measurement and anchoring devices.

SUMMARY OF THE INVENTION

The improved cranial sensor anchoring device of the present invention is inserted through a single circular hole which is drilled through the skull using a standard surgical drill. The device is characterized by a tip which in its contracted state is smaller than the hole. However, when expanded after insertion through the hole, the lateral ridges on the tip contact the inner lip of the hole at three points around its circumference preventing withdrawal of the device and assuring coplanar orientation of the tip with regard to the surface of the brain. Expansion of the tip is accomplished by rotating the second cylinder contanining the sensor. This cylinder has a cone-shaped enlargement or washer near its end which, when withdrawn into the tip of the outer cylinder during rotation as threads on the outside of this cylinder mesh with threads on the inside of outer cylinder, forces the tip of the outer cylinder to expand radially at slits cut longitudinally in the outer cylinder. The laterally projecting ridges on the tip engage the inner table of the skull around the periphery of the hole. The tip of the device, once it has been maximally withdrawn through the hole in the expanded position can only by in a tangential relationship to the surface of the brain immediately underneath the hole. With the tip of the device thus secured within the cranial cavity, a finger nut over the outer cylinder is tightened against the outer table of the skull, clamping the skull between the lateral ridges on the tip and the finger nut and preventing movement of the anchoring device in any direction. The depth of the pressure sensitive tip within the cranial cavity is thus precisely and rigidly controlled. The device thus accommodates any thickness and curvature of a normal skull, and correct placement and orientation of the pressure sensitive tip are assured, even in the face of reasonable imprecision in construction of the hole in the skull. Since the shaft of the device is smaller than the hole in the skull and does not depend on a tight fit in the hole for stability, the tip of the device will be locked in a tangential position with respect to the surface of the brain even if the hole in the skull is slightly tilted with respect to the surface of the brain. Since the lateral ridges must lock beneath the inner table of the skull, the tip of the device, once expanded, cannot be manually withdrawn through the hole. Therefore, the tip of the device if inserted according to directions, could not fail to extend through the hole in the skull and thereby fail to contact the surface of the brain, thus causing erroneous readings. Since the device does not require that threads be cut into the side of the hole for screw-type mounting, there is no danger that bone chips will be pushed ahead of the thread cutter thereby displacing the surface of the brain from the pressure sensitive tip of the transducer. The hole in the skull required to accommodate the device is a simple non-tapered, non-threaded circular hole of the type reproducibly made by standard commercially available cranial perforating drills.

The screw cap securing the transducer can be removed from the anchoring device while the anchoring device is in place. The transducer can thus be inspected, calibrated, or replaced without removing the anchoring device. Insertion and removal of a transducer now becomes independent of a surgical procedure.

BRIEF DESCRIPTION OF THE DRAWINGS

Referring more particularly to the drawings.

DETAILED DESCRIPTION OF A PREFERRED EMBODIMENT

Figure 1:
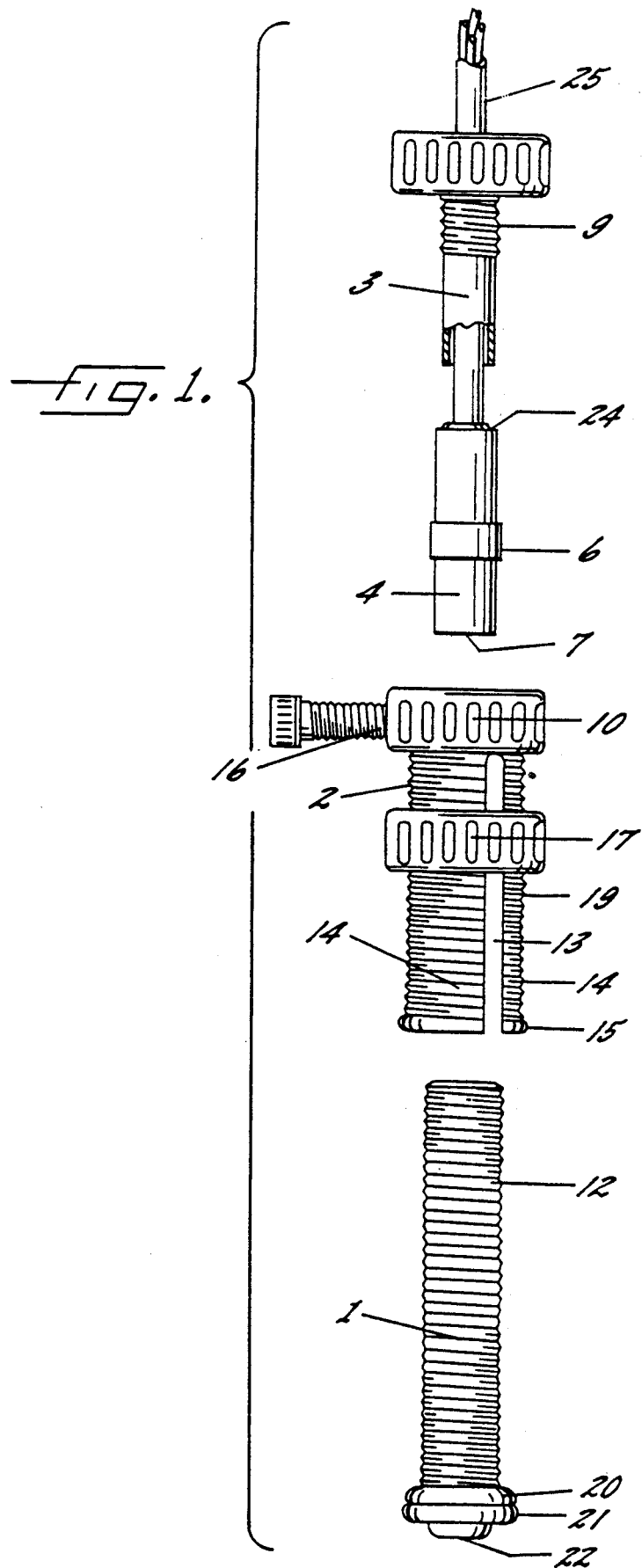
FIG. 1 is an expanded elevational view of the parts making up the presently preferred embodiment of the sensor attaching device.
Figure 2:
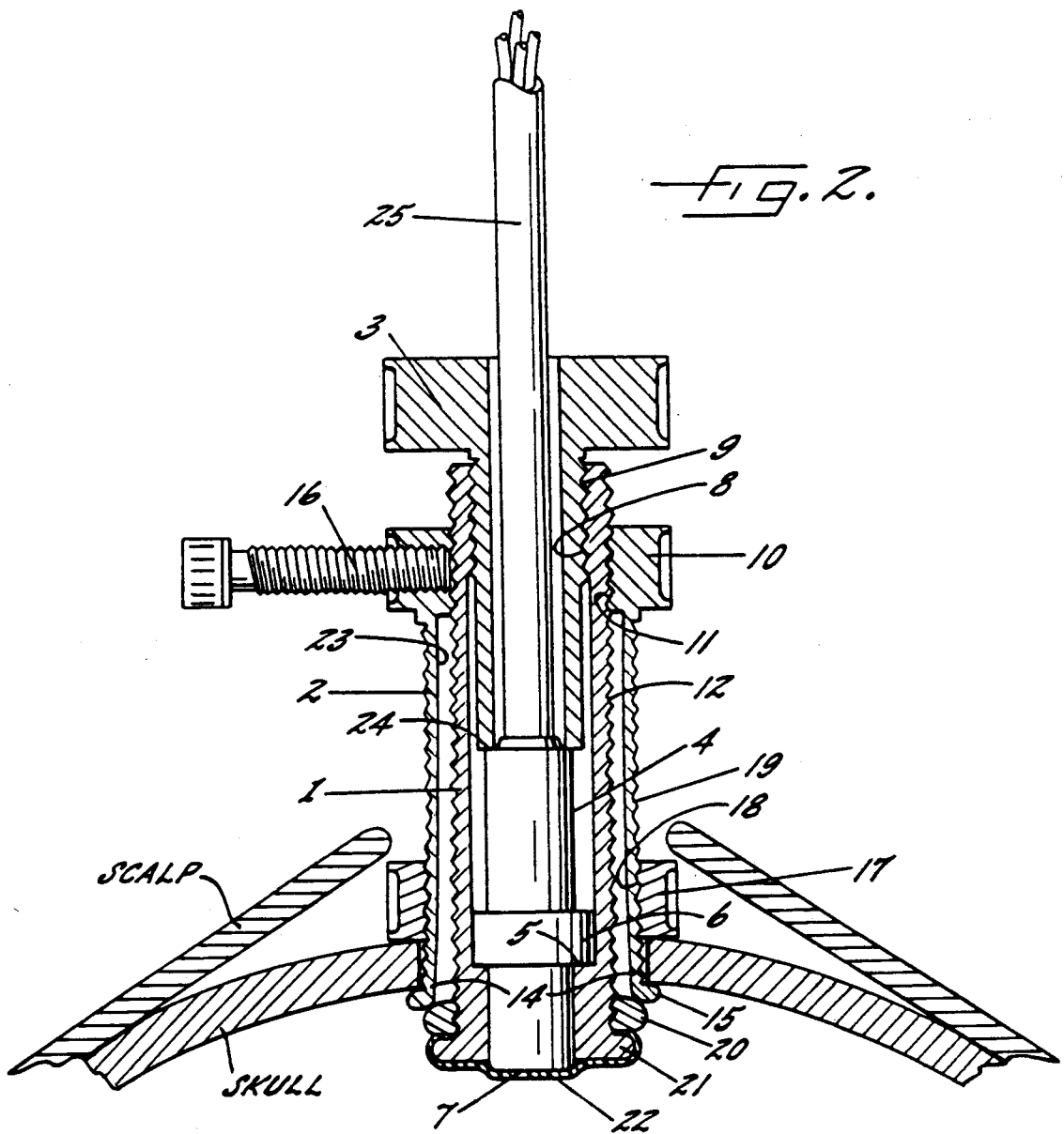
FIG. 2 is an elevation partly in section of the assembled device showing the same in position within the skull of a person with the parts being shown in slightly expanded condition for purposes of illustration. Like numerals represent like elements throughout the several views.

The device has three coaxial cylinders which, when assembled (FIG. 2) securely attach a conventional electronic sensing device to the skull. Cylinder 2 is formed as a single piece with a finger nut portion at its upper end, the interior diameter of which has threads 11 mated to outside threads 12 on cylinder 1. Below this finger nut portion 10 the inside diameter of cylinder 2 increases at 23 to that this unthreaded portion of cylinder 2 will not engage the outer threads 12 of cylinder 1.

A plurality of longitudinal slits 13 are provided in this thin walled portion of cylinder 2, creating flexible leg portions 14 which can be forced outward when cylinder 2 is screwed over cylinder 1 and the legs contact the flange 21 at the end of cylinder 1.

Cylinder 1 is formed with an exterior flange 21 at one end, and an internal shoulder 5 which reduces the inside diameter of the cylinder 1 central to this flange positioned to correspond to a shoulder 6 on a sensor 4 so that advancement of the sensor 4 through cylinder 1 is arrested at this point leaving exactly the desired amount of a sensor tip 7 protruding from cylinder 1. Above the shoulder 5 the inside of cylinder 1 is threaded at 8. This design allows the sensor 4 to be inserted inside cylinder 1 with its tip 7 protruding through flange 21. The electronic cable 25 leading from the sensor 4 passes through the center of cylinder 3, which is threaded at 9 to correspond with the threads 8 inside cylinder 1. To assemble the sensor 4 is inserted into cylinder 1, and cylinder 3 is screwed into cylinder 1 over the sensor. Thus, assembled, the tip of cylinder 3 rests on the top 24 of the sensor 4 to lock the sensor 4 securely into place.

In use, the sensor 4 is secured in place within cylinder 1, with the threads 11 within the finger nut portion of cylinder 2 engaging the outside threads 12 of cylinder 1 but the lower end of cylinder 2 not protruding over the flange 21 at the end of cylinder 1. The end of the device with the protruding pressure sensor tip can then be inserted through a hole in the skull. Cylinder 1 is then withdrawn by turning it clockwise within cylinder 2 until the legs 14 of cylinder 2 engage the flange 21 and are forced outwardly as they pass over the flange 21, expanding the diameter of the lower end of cylinder 2 so that it becomes larger than the hole in the skull and the flange portions 15 formed at the lower ends of the legs 14 of cylinder 2 meets firm resistance against the inner table of the skull when the operator attemps to withdraw the device from the hole. A set screw 16 extending through the finger nut 10 of cylinder 2 is then tightened to prevent any further rotation of cylinder 2 relative to cylinder 1, to thus hold and secure the tip of cylinder 2 in an expanded position so that the flange 15 on each of the three legs 14 of cylinder 2 engages the inner table of the skull and prevents withdrawal of the enlarged tip through the hole in the skull.

A finger nut 17 threads 18 mated to outer threads 19 on cylinder 2 is then tightened against the outer table of the skull to clamp the skull so that the anchoring device can not be moved inwardly or outwardly.

In an alternative design, to cylinder 1, may be attached a conical nut 20 which screws over the outer threads 12 of cylinder 1 and provides a compression seal of a floppy silicone rubber diaphragm 22 covering the end 7 of cylinder 1 and the exposed sensor tip 7. In operation, the rubber diaphragm 22, attached to cylinder 1 by a compression seal between the flange 21 and the conical washer 19, prevents contact of the sensor tip 7 with tissue, prevents tissue fluid from entering the interior of cylinder 1, and assures sterility of the system.

While the present invention has been described with respect to exemplary embodiments thereof, it will be understood by those of ordinary skill in the art that variations and modifications are possible within the scope and spirit of the invention.

That which we claim is:

1. A cranial sensor attaching device for securing a cylindrical end-sensitive sensor to a person's skull through a hole made in the skull so that the sensitive end of the sensor is securely positioned in tangential relationship to the brain and its covering membranes comprising:

a first cylinder having an internal device adapted to receive and hold said sensor;

said first cylinder having a flange on its lower end;

a second cylinder surrounding the first cylinder and threaded thereon, said second cylinder being slotted to provide a plurality of readily positioned flexible leg portions adapted to extend within the hole in the skull exteriorly of the lower end of the first cylinder;

means for moving the second cylinder relative to the first cylinder to cause the flange on the end of the first cylinder to expand the leg portions of the second cylinder into enlargement with the hole in the skull; and a third cylinder positioned within the first cylinder and asapted to hold the sensor securely in place within the first cylinder.

2. A cranial sensor attaching device as claimed in claim 1, wherein the mechanical intersection between the component parts of the attaching device is a screw or a ratchet.

3. A cranial sensor attaching device as claimed in claim 1 further comprising a conical nut or washer and a flexible membrane, wherein said conical nut or washer compresses said flexible membrane against said flange at the end of said first cylinder, thereby securing said membrane in position to cover the end of said first cylinder and providing a seal.

4. A cranial sensor attaching device as claimed in claim 1 wherein a threaded nut positioned by rotation along a longitudinal axis of said second cylinder provides a stop beyond which the cranial sensor attaching device cannot be advanced through the hole in the skull.

5. A cranial sensor attaching device as claimed in claim 1 wherein said third cylinder has a screw cap and is separately removable from said first cylinder when it is surgically implanted by rotating said screw cap to permit replacement of the sensor without removal of said first and second cylinders from the skull.

6. A method for securing the tip of a cylindrical sensor at desired depth and angle within the skull and permitting removal of the sensor for inspection, calibration, or replacement without a surgical procedure which utilizes a cranial sensor attaching device as claimed in claim 1 wherein a conventional and commercially available cylindrical end-sensitive pressure sensor is secured within said first cylinder so that the pressure sensitive portion of the sensor contacts the brain or its covering membrane; said first cylinder containing the sensor being inserted through a hole in the skull and secured at a precise depth within the hole by said flexible leg portions said second cylinder sliding over said first cylinder containing the sensor and secured to said second cylinder by threads or ratchet and the legs of said second cylinder being forced in a radial manner by withdrawal of said first cylinder containing the sensor through it to expand the tip of the second cylinder and prevent removal of the device from the hole; with further movement of the device being prevented by advancing a threaded nut over said second cylinder to contact the outer table of the skull.

* * * * *